United States Patent
Chang et al.

(10) Patent No.: US 10,026,620 B1
(45) Date of Patent: Jul. 17, 2018

(54) METHOD OF IRRADIATING ULTRAVIOLET LIGHT ON SILICON SUBSTRATE SURFACE FOR IMPROVING QUALITY OF NATIVE OXIDE LAYER AND APPARATUS USING THE SAME

(71) Applicant: National Applied Research Laboratories, Taipei (TW)

(72) Inventors: Mao-Nan Chang, Hsinchu (TW);
Tsung-Yu Chan, Miaoli County (TW);
Chia-Yi Wu, Kaohsiung (TW);
Chun-Ting Lin, New Taipei (TW);
Ming-Hua Shiao, Hsinchu (TW)

(73) Assignee: NATIONAL APPLIED RESEARCH LABORATORIES, Taipei (TW)

( * ) Notice: Subject to any disclaimer, the term of this patent is extended or adjusted under 35 U.S.C. 154(b) by 0 days.

(21) Appl. No.: 15/630,110

(22) Filed: Jun. 22, 2017

(51) Int. Cl.
*H01L 21/3105* (2006.01)

(52) U.S. Cl.
CPC ................ *H01L 21/3105* (2013.01)

(58) Field of Classification Search
CPC .................................................. H01L 21/3105
See application file for complete search history.

(56) References Cited

U.S. PATENT DOCUMENTS

| | | | | |
|---|---|---|---|---|
| 6,534,412 B1* | 3/2003 | Lin | ................ | H01L 21/02046 257/E21.226 |
| 2006/0099827 A1* | 5/2006 | Yoo | ................ | H01L 21/02164 438/778 |
| 2008/0026597 A1* | 1/2008 | Munro | ................ | C23C 16/401 438/788 |
| 2010/0140756 A1* | 6/2010 | Kozasa | ............ | H01L 21/02054 257/635 |
| 2012/0107607 A1* | 5/2012 | Takaki | ................ | C08J 7/047 428/336 |

* cited by examiner

*Primary Examiner* — Karen Kusumakar
(74) *Attorney, Agent, or Firm* — Jackson IPG PLLC; Demian K. Jackson

(57) ABSTRACT

The present invention relates to the growth of a native oxide layer on a surface of a silicon substrate. Deep ultraviolet (UV) light is irradiated to thereby effectively improve the quality of the native oxide layer. By improving the quality, the difficulty of the surface treatment of a cross-section sample for scanning capacitance microscopy (SCM) is improved. The life cycle and reliability of the sample are also improved with enhanced reproducibility for the measurement of SCM. Thus, the present invention provides an improved method and an apparatus using the same to prepare a cross-sectional sample for SCM. The feasibility and the concrete method for enhancing oxide layer quality on a silicon substrate surface by UV light irradiation under a humidity-controlled environment are established. The optimum parameters of irradiation time for n-type and p-type samples are made.

6 Claims, 5 Drawing Sheets

METHOD OF IRRADIATING ULTRAVIOLET LIGHT ON SILICON SUBSTRATE SURFACE FOR IMPROVING QUALITY OF NATIVE OXIDE LAYER AND APPARATUS USING THE SAME

TECHNICAL FIELD OF THE INVENTION

The present invention relates to improving the quality of native oxide layer; more particularly, to directly irradiating ultraviolet (UV) light under a humidity-controlled environment for reducing defects of the native oxide layer after being grown.

DESCRIPTION OF THE RELATED ARTS

Scanning capacitance microscopy (SCM) has been applied in the analysis of semiconductor materials and components, where the most important application is the analysis of metal-oxide-semiconductor field-effect transistor (MOSFET). Mostly, the analysis is done through observing the images of two-dimensional carrier distribution and pn junctions. Recently, the application studies include the photoresponse in pn junctions of indium gallium arsenide (InGaAs) (Hui Xia, Tian-Xin Li, Heng-Jing Tang, Liang Zhu, Xue Li, Hai-Mei Gong, and Wei Lu, "Nanoscale imaging of the photoresponse in PN junctions of InGaAs infrared detector", Scientific Reports 6, 21544 (2016)) and the observation of Anderson localization on graphene (Y. Naitou and S. Ogawa, "Anderson localization of graphene by helium ion irradiation", Appl. Phys. Lett. 108, 171605 (2016)).

The basic principle of SCM is that, by using a conductive probe and a silicon substrate sample, a metal-oxide-semiconductor (MOS) structure is formed. In FIG. 4, a small alternating voltage, so-called modulation voltage, is applied at the end of a sample. This slight change of voltage (dV) causes a slight change of capacitance (dC) in the MOS structure, where a differential capacitance signal (DC/dV) is thus obtained as the slope of capacitance-voltage curve. The differential capacitance signal will show information about the doped type and concentration of the sample.

SCM is applied to detect and analyze the electrical features of a silicon substrate semiconductor. The key factor which affects this analysis is the preparation of the sample. The sample preparation is an important step that affects the quality of SCM sample. Therein, the quality of oxide layer is the key. The quality of the oxide layer on a surface of the sample directly affects the signal strength and reproducibility of SCM. Through general oxidation methods used in semiconductor industries, such as thermal oxidation and wet oxidation, oxide layers with good quality can be obtained.

For the growth of silicon oxide ($SiO_2$), there is a corresponding international patent H01L21/02274: An insulating material is formed on a substrate, characterized in that a layer of the insulating material is formed through vapor deposition or through decomposing or reacting with gas-phase compound, i.e. chemical vapor deposition (CVD) in the presence of plasma—plasma-enhanced chemical vapor deposition (PECVD).

However, in prior arts, there are few cases in which the light-assisted growth of $SiO_2$ is used in an atmospheric environment, but CVD is more often applied. As disclosed in U.S. Pat. No. 4,988,533 A, silane is used in a plasma environment with UV light irradiated for growing a $SiO_2$ layer. Regarding the interaction of light and silicon native oxide layer, there are prior arts of removing the native oxide layer by using light irradiation. In FIG. 5, for example, U.S. Pat. No. 6,534,412 B1 discloses that a UV laser is irradiated on a surface of a sample in a controlled environment to remove native oxide layer with introduction of hydrogen.

Since most SCM applications are mainly for cross-section analysis, it is often necessary to prepare a cross-section sample. But for preparing a cross-section sample for SCM, the traditional semiconductor process used for growing oxide layer is full of difficulties and challenges, The cost is high, nor the analysis fast enough. Hence, the prior arts do not fulfill all users' requests on actual use.

SUMMARY OF THE INVENTION

The main purpose of the present invention is to irradiating UV light under a humidity-controlled environment for reducing the defects of native oxide layer after being grown, where the native oxide layer of a silicon-substrate cross-section sample directly obtains improved quality for good and stable SCM signals.

Another purpose of the present invention is to provide a fast and low-cost method and apparatus to help the growth of a native oxide layer on a surface of a silicon substrate, where the quality of the native oxide layer on the surface of the silicon substrate is effectively improved; the difficulty of the surface treatment of a cross-section sample is greatly reduced; the life cycle and reliability of the sample are improved; and the reproducibility of SCM measurement is enhanced.

To achieve the above purposes, the present invention is a method of irradiating UV light on a silicon substrate surface for improving the quality of a native oxide layer, comprising steps of: (a) obtaining a to-be-treated sample of a silicon substrate; and (b) irradiating cross section of the to-be-treated sample with UV-light under a low-water-vapor environment, where the to-be-treated sample is irradiated with UV light of a wavelength of 180 nanometers (nm)~400 nm under the low-water-vapor environment having a relative humidity less than 40 percents (%). Accordingly, a novel method of irradiating UV light on a silicon substrate surface for improving the quality of a native oxide layer is obtained.

BRIEF DESCRIPTION OF THE DRAWINGS

The present invention will be better understood from the following detailed description of the preferred embodiment according to the present invention, taken in conjunction with the accompanying drawings, in which.

DESCRIPTION OF THE PREFERRED EMBODIMENT

The following description of the preferred embodiment is provided to understand the features and the structures of the present invention.

Figure 1:
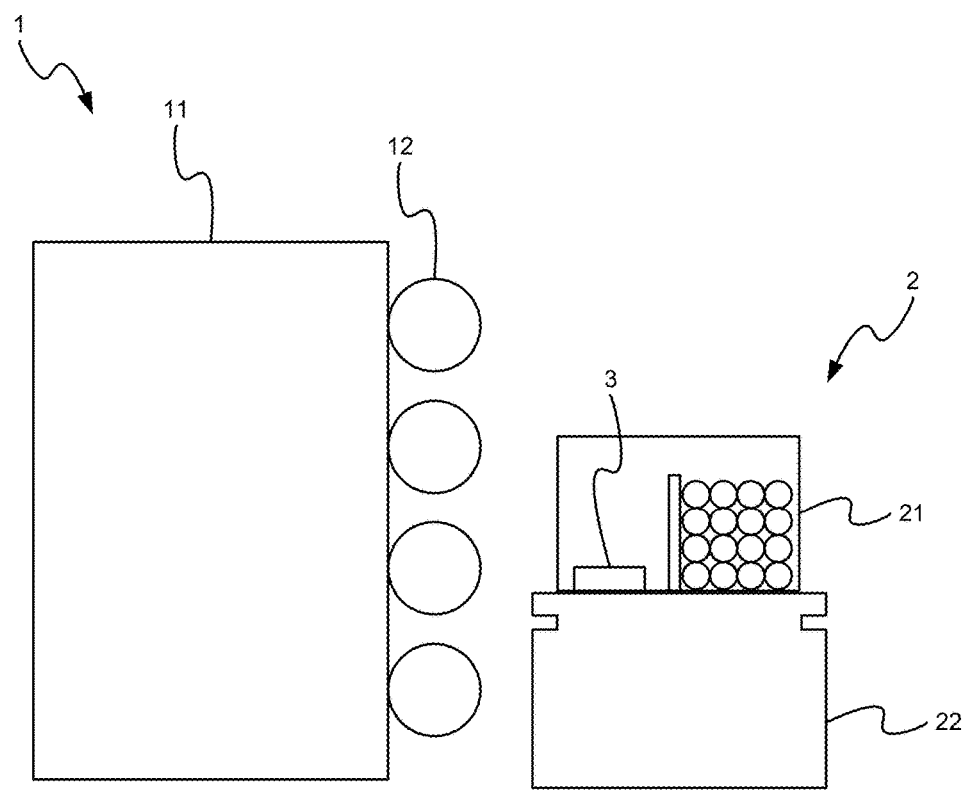
FIG. 1 is the structural view showing the apparatus used in the preferred embodiment according to the present invention.
Figure 2:
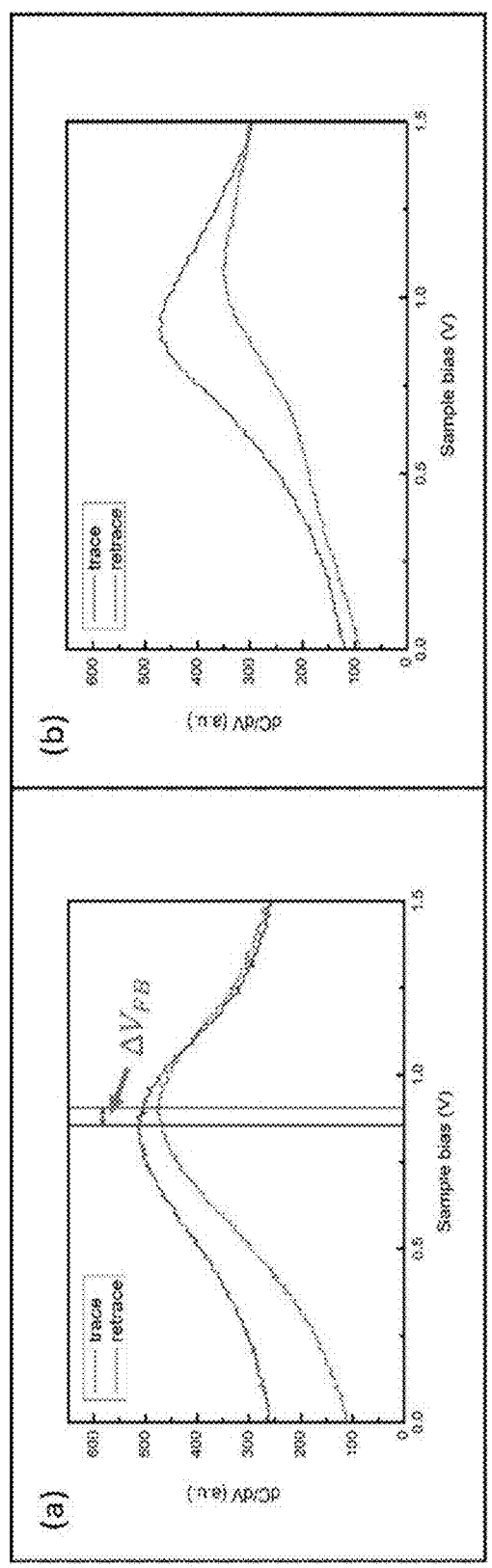
FIG. 2 is the view showing the scanning capacitance spectroscopy (SCS) of the native oxide layers irradiated and not irradiated by ultraviolet (UV) light of the specific wavelength, separately.
Figure 3:
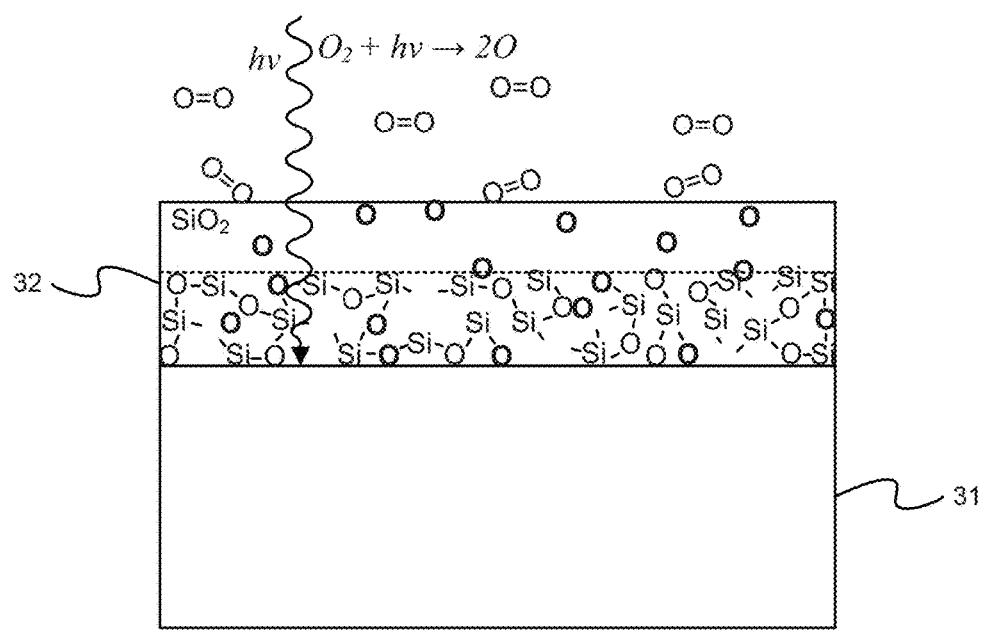
FIG. 3 is the view showing the native oxide layer irradiated by UV light of the specific wavelength.
Figure 4:
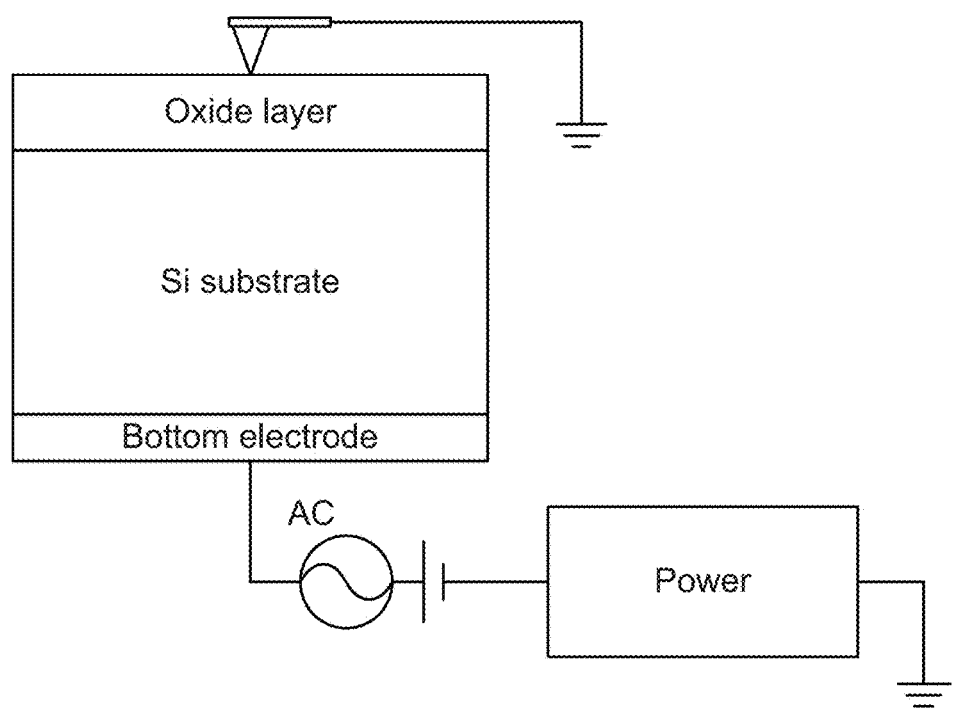
FIG. 4 is the circuit view of scanning capacitance microscopy (SCM)
Figure 5:
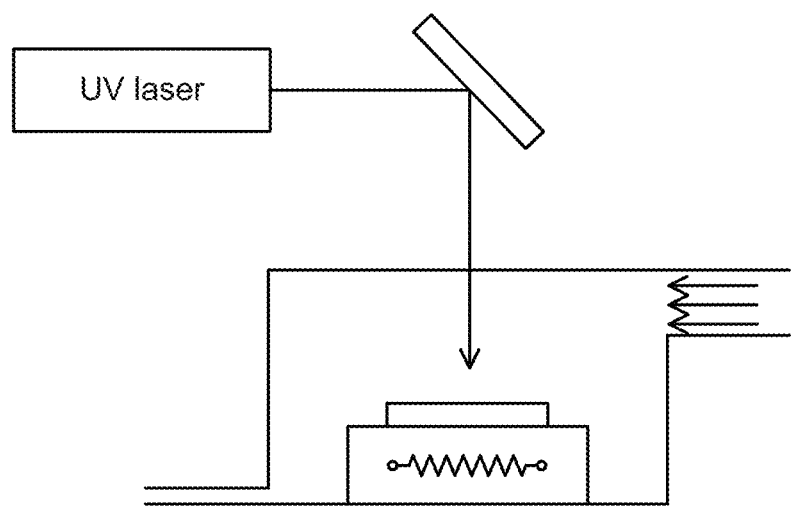
FIG. 5 is the view of the use of UV laser used for removing the native oxide layer.

Please refer to FIG. 1~FIG. 3, which are a structural view showing an apparatus used in a preferred embodiment according to the present invention; a view showing SCS of native oxide layers irradiated and not irradiated by UV light of a specific wavelength, separately; and a view showing a native oxide layer irradiated by UV light of the specific wavelength. As shown in the figures, the present invention is a method of irradiating UV light on a silicon substrate surface for improving the quality of native oxide layer.

The present invention proposes a rapid and low-cost apparatus and method for improving the quality of a native oxide layer on a surface of a silicon substrate by UV light irradiation. Deep UV light irradiation is used for assisting the growth of the native oxide layer on the surface of the silicon substrate; and thus effectively improving the quality of the native oxide layer and greatly reducing the difficulty on the surface treatment of the cross section of a sample. Besides, the life cycle and reliability of the sample are improved while the reproducibility of SCM measurement is enhanced. Hence, the present invention is suitable for testing a silicon semiconductor sample. The apparatus used in the present invention comprises a UV-light source 1 and a humidity-controlled environment 2.

The UV-light source 1 irradiates UV light of a wavelength of 180 nanometers (nm)~400 nm, which comprises a lamp holder and a plurality of UV-light tubes 12 located on the lamp holder.

The humidity-controlled environment 2 is connected to the UV-light source 1 to carry a to-be-treated sample 3 to be exposed under UV light irradiation. The UV-light source 1 is set in the humidity-controlled environment 2 to directly irradiate the cross section of the to-be-treated sample 3. The humidity-controlled environment 2 has a relative humidity less than 40 percents (%); and comprises a sealed quartz box 21 and a lifting platform 22 carrying the sealed quartz box 21. The sealed quartz box 21 holds the to-be-treated sample 3 under a dry environment having the relative humidity formed by using a desiccant or vacuum-sucking.

On using the present invention, the UV-light tubes 12 (4 watts (W), 254 nanometers (nm)) are used to irradiate the cross section of the to-be-treated sample 3 under the humidity-controlled environment 2. A comparison is made between the native oxide layers irradiated by UV light for 2 hours and not irradiated by UV light, separately. The SCS diagrams are shown in FIG. 2, where diagram (a) shows the result for 2-hour irradiation and diagram (b) for no irradiation. As is shown, the sample irradiated with UV light has a smaller flat-band voltage shift, together with a slighter variation of SCS curve, than the sample not irradiated. The size and direction of the flat-band voltage shift represent the trap charge amount and charge polarity in oxide layer. The trap charge amount indicates the quality of oxide layer—the more the trap charge amount, the worse the quality. As is shown in the experiment data, the sample irradiated by UV light has an oxide layer with better quality. The present invention also finds that, when the curve of the flat-band voltage shift is positive, main trap charge represents hole, which is consistent with substrate type and bias direction.

In FIG. 3, the present invention uses UV light to improve the quality of a native oxide layer on a surface of a to-be-treated sample 3. Generally, the surface of a silicon substrate 31 will have a native oxide layer 32 poor in quality and defective. Hence, the layer is generally etched during fabrication and, then, a more perfect oxide layer will be grown instead. However, when UV light is irradiated on the surface of the to-be-treated sample 3, the energy of UV light makes surrounding oxygen molecules decomposed into oxygen atoms. Because there are six electrons in its shell domain, the oxygen atom has ability to further capture electrons and fill vacancy in the native oxide layer 32. UV light decomposes the oxygen molecules into oxygen atoms; the concentration of the oxidant (oxygen atom) increases; the oxidation reaction is enhanced; and the $SiO_x$ structure of the native oxide layer 32 is changed into a $SiO_2$ structure with the quality of the oxide layer made better.

The present invention improves the technology of preparing a cross-section sample for SCM, where a method is proposed for improving the quality of a native oxide layer on a surface of a silicon substrate by irradiating UV light. The preparation of the SCM sample uses no semiconductor manufacture equipments, while the difficulty in the surface treatment of the cross-section sample is effectively reduced and the life cycle of the sample and the reproducibility of SCM measurement are improved too. It is pointed out from the experiment data that, as compared to a general native oxide layer, the native oxide layer on the surface of a p-type sample has the improvement rates of oxide-layer defects and interface defects about 73.54% and 68.98% after 2 hours of deep UV light irradiation, respectively. Therein, the improvement rate of oxide-layer defects is rather obvious; and, the wavelength of UV light has higher effect on the quality of oxide layer than the intensity of UV light. Concerning the life cycle of the native oxide layer, the decay rate of oxide-layer defects and interface defects are about 12.73% and 8.723% after the sample are placed still for two days. In the present invention, the feasibility and the concrete method for enhancing the oxide layer quality on a silicon substrate surface by ultraviolet light irradiation are established. Furthermore, the optimum parameters of the irradiation time for n-type and p-type samples are made, where the preparation of a silicon substrate sample for SCM can be made easier. Especially for cross-section samples, technical difficulties and challenges for growing oxide layer by using on using semiconductor manufacture equipments are reduced. Hence, in the future, the analysis of a silicon substrate sample for SCM can be stable and reliable. The present invention uses direct UV light irradiation under a humidity-controlled environment to reduce the defects of a native oxide layer after growth, which can be applied in cross-section sample detection but not yet disclosed by prior arts.

To sum up, the present invention is a method of irradiating UV light on a surface of a silicon substrate for improving the quality of a native oxide layer and an apparatus using the same, where the preparation of a cross-section sample for SCM is improved; the feasibility and the concrete method for enhancing oxide layer quality on a silicon substrate surface by UV light irradiation under a humidity-controlled environment are established; the optimum parameters of irradiation time for n-type and p-type samples are made; the present invention greatly improves the stability and reliability of the analysis of a silicon substrate sample for SCM; and the present invention can be directly applied in the cross-section detection of an integrated circuit sample.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. A method of irradiating ultraviolet (UV) light on a silicon substrate surface comprising steps of:

(a) obtaining a to-be-treated sample of a silicon substrate and
(b) directly irradiating a cross section of said to-be-treated sample with UV-light of a wavelength of 180 nanometers (nm)~400 nm under a low-water-vapor environment having a relative humidity less than 40 percents (%) so as to change a $SiO_x$ structure of a native oxide layer of the to-be-treated sample to a $SiO_2$ structure.

2. The method according to claim 1, wherein, after processing said steps, defects of said native oxide layer of said to-be-treated sample is reduced.

3. The method according to claim 1, wherein said method uses an apparatus comprising
   a UV-light source irradiating UV light of 180-400 nm; and
   a humidity-controlled environment connected to said UV-light source, wherein said humidity-controlled environment carries said to-be-treated sample to be exposed under irradiation of said UV-light source.

4. The method according to claim 3, wherein said humidity-controlled environment comprises a sealed quartz box and a lifting platform; said lifting platform carries said sealed quartz box; and said sealed quartz box holds said to-be-treated sample under a relative humidity less than 40%.

5. The method according to claim 4, wherein said sealed quartz box obtains said relative humidity by a method selected from a group consisting of using a desiccant and vacuum-sucking.

6. The method according to claim 3, wherein said UV-light source comprises a lamp holder; and a plurality of UV-light tubes located on said lamp holder and each configured to irradiate 254 nm UV light at 4 W.

\* \* \* \* \*